US00PP29677P3

(12) United States Plant Patent
Lugli et al.

(10) Patent No.: US PP29,677 P3
(45) Date of Patent: Sep. 18, 2018

(54) CHERRY TREE NAMED 'PA6UNIBO'

(50) Latin Name: ***Prunus avium* L.**
Varietal Denomination: PA6UNIBO

(71) Applicant: Alma Mater Studiorum—Università di Bologna, Bologna (IT)

(72) Inventors: Stefano Lugli, Bologna (IT); Riccardo Correale, Bologna (IT); Michelangelo Grandi, Bologna (IT)

(73) Assignee: Alma Mater Studiorum—Università di Bologna, Bologna (IT)

( * ) Notice: Subject to any disclaimer, the term of this patent is extended or adjusted under 35 U.S.C. 154(b) by 0 days.

(21) Appl. No.: 15/330,470

(22) Filed: Sep. 22, 2016

(65) Prior Publication Data

US 2017/0118881 P1 Apr. 27, 2017

Related U.S. Application Data

(60) Provisional application No. 62/284,255, filed on Sep. 23, 2015.

(51) Int. Cl.
*A01H 5/08* (2018.01)

(52) U.S. Cl.
USPC ..... Plt./181
CPC ..... *A01H 5/085* (2013.01)

(58) Field of Classification Search
USPC ..... Plt./156, 180, 181
See application file for complete search history.

*Primary Examiner* — Susan McCormick Ewoldt
*Assistant Examiner* — Karen M Redden
(74) *Attorney, Agent, or Firm* — Michelle Bos Legal LLC

(57) ABSTRACT

'PA6UNIBO' is a new cherry tree variety selected for its vigorous growth and excellent yield, as well as its attractive dark red, flavorful fruit.

3 Drawing Sheets

Variety denomination: 'PA6UNIBO'.
Genus and species: *Prunus avium* L.

BACKGROUND AND SUMMARY OF THE VARIETY

'PA6UNIBO' cherry tree, originally derived from a seedling of unknown parentage and called Selection DCA BO B5 D20, was first discovered in 2000 at Vignola, Modena Province, Italy and planted in 2002 at the same location. The first crop was obtained in 2004. 'PA6UNIBO' was first propagated by grafting at Vignola, Modena Province, Italy in 2008 on 'Colt' (U.S. Plant Pat. No. 4,059) and 'CAB 6P' (not patented) root stocks of differing vigor in trial fields, to test growth and yield performance under differing training systems and planting densities. The variety was found to have the properties proper to a promising new cultivar for the market, and has been found to retain its distinctive characteristics and reproduce true-to-type through successive asexually propagated generations. 'PA6UNIBO' picks 10 to 12 days after 'Burlat' (not patented) and 8 to 10 days before 'Bing' (not patented).

Compared to Celeste® 'Sumpaca' (not patented) cherry tree, the fruit of 'PA6UNIBO' are larger, heart-shaped, of firmer flesh, with longer stem, more uniform ripening, and higher sugar content.

'PA6UNIBO' cherry tree was selected for its high qualities, including tree growth and yield performance, and fruit appearance and excellent taste-flavor properties.

BRIEF DESCRIPTION OF THE PHOTOGRAPHS

DETAILED BOTANICAL DESCRIPTION OF THE VARIETY

Figure 1:
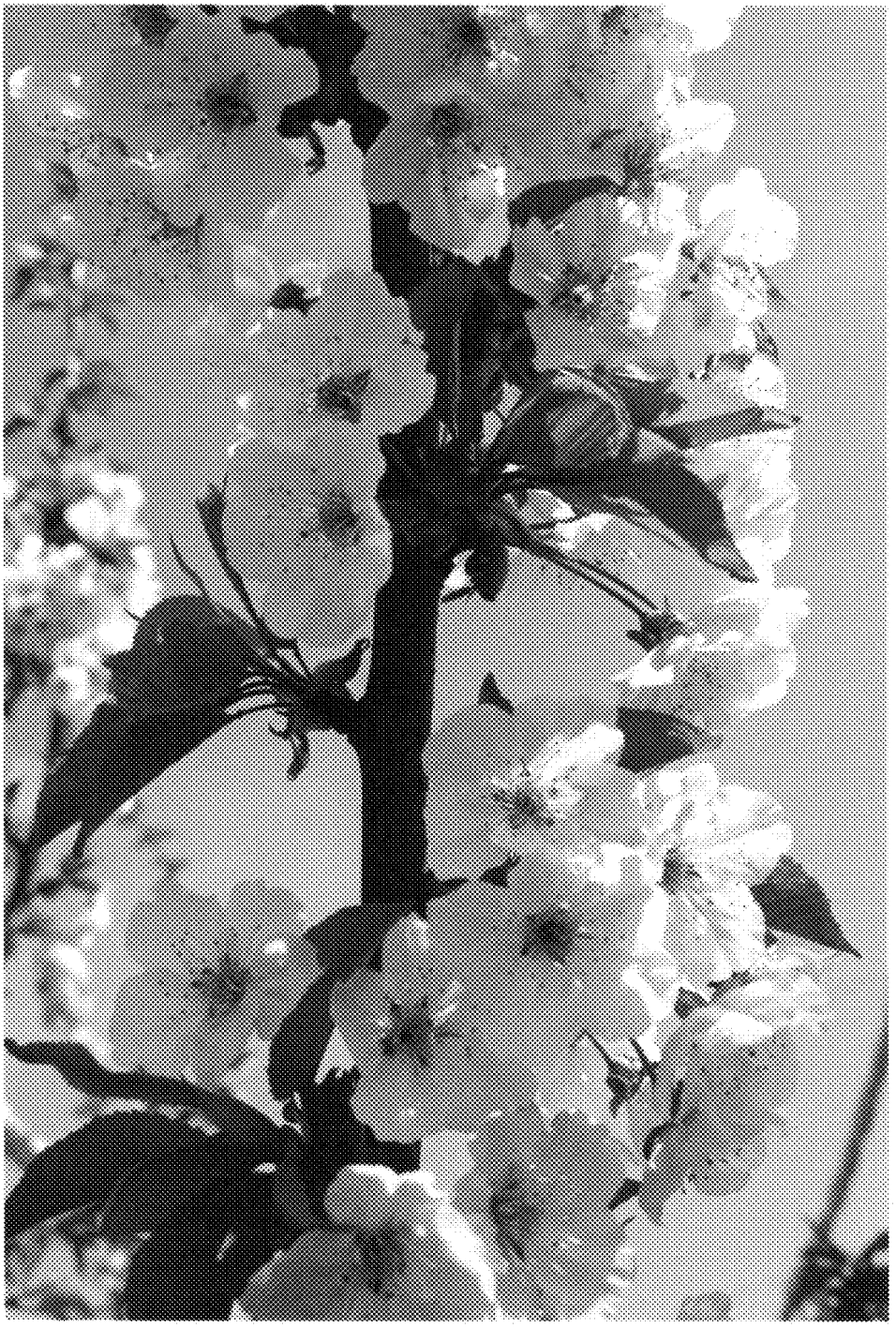
FIG. 1 shows detail of full bloom of an 8-year-old 'PA6UNIBO' cherry tree.
Figure 2:
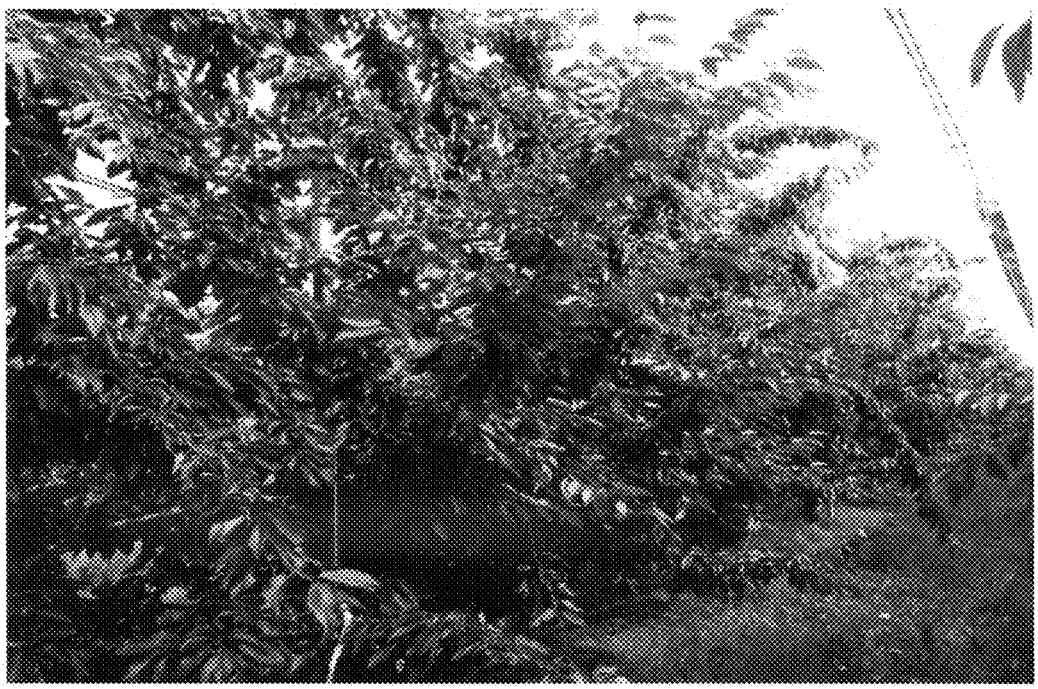
FIG. 2 shows the habit of an 8-year-old 'PA6UNIBO' cherry tree.
Figure 3:
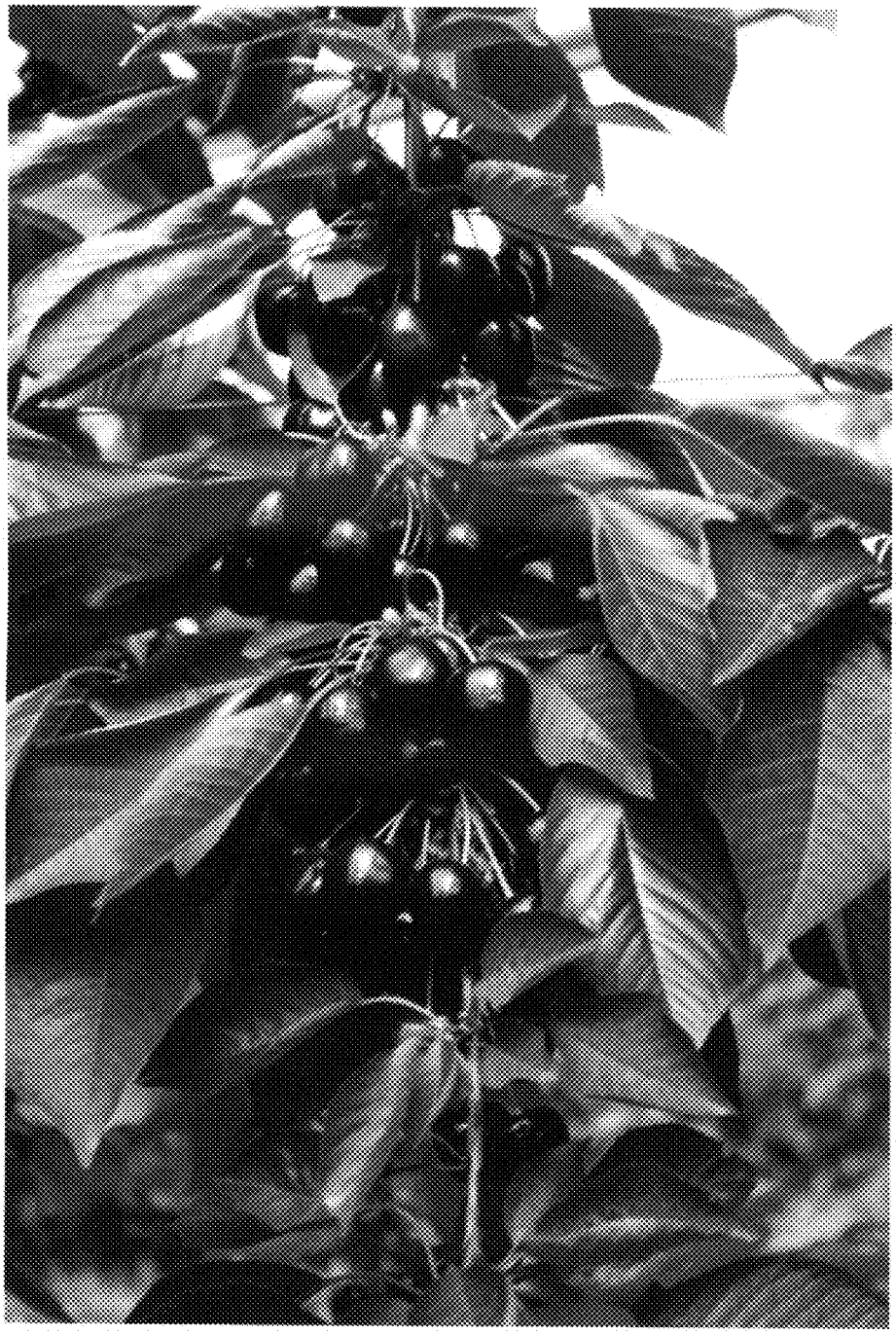
FIG. 3 shows detail of 'PA6UNIBO' fruit and leaves.

The following is a detailed botanical description of 'PA6UNIBO' cherry tree, based on observations of 8-year-old trees made during the 2015 growing season at Vignola, Modena Province, Italy. All colors are described according to The Royal Horticultural Society Colour Chart ($5^{th}$ Edition, 2007). It should be understood that the botanical and analytical characteristics described will vary somewhat depending upon cultural practices and climatic conditions, and can vary with location and season. Quantified measurements are expressed as an average of measurements taken from a number of individual plants of the new variety. The measurements of any individual plant, or any group of plants, of the new variety may vary from the stated average Tree:

*Vigor.*—High; more vigorous than 'Kordia' (not patented), less vigorous than 'Regina' (not patented).
*Height.*—4.5 meters.
*Spread.*—3 meters.
*Growth habit.*—Semi-upright.
*Canopy density.*—Medium.
*Trunk diameter at about 25 cm height, measured at about 5 cm above graft joint.*—
*Trunk color.*—Reddish-brown 200C.
*Bark texture.*—Slightly rough.
*Tendency toward alternate bearing.*—No.
*Winter hardiness.*—Unknown, no cold damage found in Po Valley district where grown.
*Chilling requirement.*—Unknown.

Branch:
*Length.*—250 cm to 300 cm.
*Diameter.*—5 cm to 7 cm.
*Crotch angle.*—35° to 50° depending on training system.
*Bark color.*—Reddish-Brown 200C.
*Bark texture.*—Slightly rough.

Current year shoot:
*Length.*—50 cm to 60 cm.
*Color.*—Reddish-brown 200D with fairly widespread gray 201A overtone.

Flower bud:
*Number per spur.*—3 to 4.
*Shape.*—Sub-globose.
*Length.*—About 1 cm.
*Diameter.*—Under 1 cm.
*Color.*—Reddish perules 187C.

Flower:
*Number per cluster.*—Minimum 8, maximum 10 per spur; 2 to 3 per bud. Bloom is abundant.
*Relative position of petals.*—Petals overlap slightly.
*Diameter.*—35 mm to 42 mm.
*Depth.*—10 mm to 13 mm, measured as distance from receptacle to maximum petal aperture.
*Pollen.*—Present, color yellow 12C; self-fertile.

Sepal:
*Length.*—6 mm to 8 mm.
*Shape.*—Slightly pointed, tending to lanceolate.
*Width.*—4 mm to 5 mm.
*Apex.*—Pointed.
*Base.*—Flat.
*Quantity.*—5.
*Margin.*—Regular. Color — upper surface: Pale green 138C. Color — lower surface: Pale green 138C with reddish venation 182A.

Petal (when flower is fully open):
*Number per flower.*—5.
*Shape.*—Circular.
*Length.*—18 mm to 20 mm.
*Width.*—14 mm to 16 mm.
*Apex.*—Slightly sunken.
*Base.*—Pointed.
*Margin.*—Slightly undulated.
*Texture.*—Smooth. Color — upper surface: White 155B. Color — lower surface: White 155B.

Bloom:
*Date of bud burst.*—March 19 to 20, 2014.
*Date of first bloom.*—Mar. 26, 2014.
*Date of full bloom.*—Mar. 30, 2014.

Pedicel:
*Length.*—32 mm to 36 mm.
*Diameter.*—About 1.0 mm.
*Color.*—Pale green 146D.

Pistil:
*Quantity.*—1.
*Size.*—15 mm to 18 mm.
*Color.*—Pale green 145B.

Anthers:
*Quantity.*—26 to 32.
*Length.*—5 mm to 8 mm, outer anthers longer than inner anthers.
*Diameter.*—About 1 mm.
*Color.*—Orange-yellow 15B with white filament (155D).

Stigma:
*Quantity.*—1.
*Size.*—0.9 mm to 1.1 mm diameter.
*Color.*—Pale green 145B.

Style:
*Quantity.*—1.
*Size.*—9 mm to 12 mm length.
*Color.*—Green 150C at basal part, darker green 149C at distal part.

Ovary:
*Quantity.*—1.
*Size.*—4 mm to 6 mm.
*Color.*—Green 144A.

Leaves:
*Arrangement.*—Alternate.
*Venation.*—Reticulate.
*Length.*—13.0 cm to 14.0 cm.
*Width.*—7.0 cm to 8.0 cm.
*Shape.*—Lanceolate-elliptical.
*Apex shape.*—Pointed.
*Base shape.*—Pointed.
*Upper surface texture.*—Smooth.
*Lower surface texture.*—Ribbed.
*Margin.*—Serrate, fine toothed.
*Upper surface color, mature leaf.*—Dark green 137B.
*Lower surface color, mature leaf.*—Green-yellow 147B.
*Nectaries.*—Length 2 to 3 mm; width 1 to 2 mm.
*Stipules.*—2 per leaf; length 7 to 10 mm; green-yellow 148B.

Petiole:
*Length.*—3.8 cm to 4.5 cm.
*Diameter.*—About 1.5 mm.
*Color.*—Lower, green-yellow 148B; upper reddish 187B.

Fruit:
*Shape.*—Heart-shaped.
*Diameter.*—Mostly 30 mm.
*Height.*—23 mm to 27 mm.
*Weight.*—12 g to 14 g on average.
*Number per cluster.*—4 to 8 per spur.
*Skin color.*—Shiny dark red 187B tending to blackish-dark red 187A at advanced maturity.
*Lenticels density.*—Medium-high.
*Skin thickness.*—Thin.
*Skin texture.*—Smooth.
*Tendency to crack.*—Medium-low.
*Anthocyanin coloration near skin.*—None.
*Tenacity of flesh to stone.*—Medium-low.
*Flesh color.*—Red 53A.
*Flesh texture.*—Fine.
*Juiciness.*—High.
*Juice analysis.*—17.6° Brix and 9.9 g/l malic acid (2011-2014 data).
*Stone size.*—Medium.
*Stone shape.*—Elliptical.
*Stone color.*—Pale brown 165D.

Fruit stem:
*Length.*—40 mm to 50 mm.
*Diameter.*—Just over 1 mm.
*Color.*—Green 143A.

Harvest:
*Maturity and harvest date range.*—10 to 12 days after 'Burlat' (8 to 10 days before Bing).
*Productivity.*—15 to 20 tons per hectare.

Market use: Fresh market.

We claim:

1. A new and distinct variety of cherry tree, substantially as illustrated and described herein.

* * * * *